US010518047B2

(12) United States Patent
Huang et al.

(10) Patent No.: US 10,518,047 B2
(45) Date of Patent: Dec. 31, 2019

(54) ELECTROSPRAY ATOMIZING DEVICE THAT SPRAYS AT A CONSTANT RATE

(71) Applicant: Elite Secret Biotechnology Corp., Taipei (TW)

(72) Inventors: Tien-Yao Huang, Taipei (TW); Chin-Hong Tsai, Taipei (TW)

(73) Assignee: ELITE SECRET BIOTECHNOLOGY CORP., Taipei (TW)

( * ) Notice: Subject to any disclaimer, the term of this patent is extended or adjusted under 35 U.S.C. 154(b) by 84 days.

(21) Appl. No.: 15/946,136

(22) Filed: Apr. 5, 2018

(65) Prior Publication Data

US 2018/0311447 A1 Nov. 1, 2018

(30) Foreign Application Priority Data

Apr. 26, 2017 (TW) ............................ 106114010 A

(51) Int. Cl.

*B05B 5/035* (2006.01)
*B05B 1/02* (2006.01)
*A61M 15/02* (2006.01)
*A61M 11/00* (2006.01)
*A61M 11/04* (2006.01)
*A61M 35/00* (2006.01)

(52) U.S. Cl.
CPC ......... *A61M 11/044* (2014.02); *A61M 11/007* (2014.02); *A61M 15/02* (2013.01); *A61M 35/003* (2013.01); *B05B 1/02* (2013.01); *B05B 5/035* (2013.01); *A61M 2205/103* (2013.01)

(58) Field of Classification Search
CPC .............. A61M 11/006; A61M 11/007; A61M 11/044; A61M 15/02; A61M 35/003; A61M 2205/103; A61M 2205/106; B05B 1/02; B05B 5/035; B05B 5/1691
See application file for complete search history.

(56) References Cited

U.S. PATENT DOCUMENTS

| | | | | |
|---|---|---|---|---|
| 2009/0088700 A1* | 4/2009 | Imbayashi | ............ | A61M 15/02 604/181 |
| 2010/0059608 A1* | 3/2010 | Obata | .................... | A45D 44/00 239/690 |

* cited by examiner

*Primary Examiner* — Darren W Gorman
(74) *Attorney, Agent, or Firm* — Muncy, Geissler, Olds & Lowe, P.C.

(57) ABSTRACT

An electrospray atomizing device that sprays at a constant rate comprises a main unit containing a circuit board, an electrode plate, liquid tanks and syringes. The electrode plate includes the sealed liquid tanks and the syringes, and the circuit board connects electric current to the electrode plate and the syringes. The present invention further includes a power mechanism and a dosing device. The power mechanism drives a screw to ascend or descend, pushing the pistons of the dosing device through a speed changer. The syringes are connected with the liquid tanks. When the pistons are linked by the power mechanism and the speed changer to ascend, the liquid in the liquid tanks is sprayed at a constant rate through the syringes, forming mist which carries negative ions. When the pistons descend, the ambient liquid is sucked into the liquid tanks through the syringes, waiting for a next electrospray.

8 Claims, 7 Drawing Sheets

ELECTROSPRAY ATOMIZING DEVICE THAT SPRAYS AT A CONSTANT RATE

BACKGROUND OF THE INVENTION a) Field of the Invention

The present invention relates to an electrospray atomizing device that sprays at a constant rate, and more particularly to an electrospray atomizing device that sprays at a constant rate, wherein essence concentrate for facial or skin care is sprayed on the skin after nano-electrospray ionization, so that the essence concentrate can be absorbed by the skin easily. In addition, the shortcoming in a conventional electrospray atomizing device that it cannot spray at a constant rate can be removed, and the essence concentrate that is nanosized and carries negative ions can be sprayed out at a constant rate at each electrospray.

b) Description of the Prior Art

It is known that the essence concentrate is liquid used often to care the skin, and most of the essence concentrate contains high efficient and stable antioxidant to repair damaged skin gradually, forming healthy and tightened skin. In addition, the redness to the skin can be mitigated and the skin can be whitened. Besides that, as the essence concentrate is also capable of moisturizing the skin, it becomes an indispensable care product for modern ladies who love for attractiveness. A common way of using the essence concentrate is to interfuse the essence concentrate into a skincare facial mask and cover the skincare facial mask on a human face or skin to care the skin. However, it wastes time and labor to cover the facial mask on the face or skin, and people will need to wait for quite a long time for the essence concentrate to take effect, which causes a lot of inconveniences. In addition, immersing the essence concentrate in the skincare facial mask cannot develop the function of the essence concentrate, mainly due to that the water molecules in the essence concentrate are large that they cannot infiltrate into the skin. Therefore, the facial mask can be only used to retain moisture temporarily and does not have other anti-oxidizing function, not showing effectiveness in use for many people.

Furthermore, for an existing device that sprays the essence concentrate on the human skin, the essence concentrate is vibrated in high frequency to form mist and is then sprayed on the skin. The atomized spraying can save a lot of time without a need to put on the facial mask for a long time. However, the water molecules in the atomized mist after the high frequency vibration are still large and cannot be absorbed by the skin. Therefore, the practical effect is not significant and is still used to moisturize the skin temporarily. The essence concentrate can be also sprayed on the skin by electrospray, wherein the droplets of the essence concentrate are undergone with negative ionization by high voltage and the essence concentrate that is negative ionized will be nanosized and form fine atomized molecules which are then sprayed on the skin, so that the fine atomized molecules in the essence concentrate can be interfused into the skin, achieving a better effect as they are easily absorbed by the skin. However, each time when an electrospray atomizer sprays the essence concentrate on the skin, the amount of spray cannot be controlled, and a user cannot master the inventory and the amount of spray of the essence concentrate. In addition, if the essence concentrate is stored in the atomizer, the inventory of the essence concentrate in the atomizer is limited and the essence concentrate can be contaminated easily, resulting in a lot of trouble in use.

SUMMARY OF THE INVENTION

The conventional skincare facial mask can only be used to retain moisture temporarily without developing the function of the essence concentrate therein. In addition, there is no other anti-oxidizing function. Furthermore, if the essence concentrate is sprayed on the skin using the atomizer, as the molecules of the essence concentrate are large, each spray cannot be controlled at a constant rate.

Accordingly, the present invention discloses an electrospray atomizing device that sprays at a constant rate, comprising a main unit which contains a transformer, a circuit board, an electrode plate, plural liquid tanks and plural syringes. An interior of the electrode plate is provided with the plural liquid tanks, the syringes are disposed above the liquid tanks, the liquid tanks contain liquid water, and the circuit board connects electric current to the electrode plate and the syringes. When the liquid water flows through the syringes, it will become mist and carry negative ions. The present invention is characterized in that the electrospray atomizing device includes a power mechanism and a dosing device. The power mechanism is provided with a motor, the motor is provided with a transmission shaft, the transmission shaft rotates a speed changer, the speed changer drives a screw to ascend or descend, and an upper side of the screw is pivoted with and abutted to a push board.

In the dosing device, a piston is disposed on a bottom of a liquid tank, and a top board is disposed on a top of a liquid tank to seal the liquid tank. A syringe is disposed above the top board and is connected with a liquid tank. The piston is linked by the push board to ascend or descend. When the pistons ascend by the power mechanism, the liquid in the liquid tanks is sprayed out through the syringes, forming mist which carries negative ions. On the other hand, when the pistons descend by the power mechanism, the ambient liquid is sucked into the liquid tanks through the syringes to wait for a next electrospray.

The primary object of the present invention is to provide an electrospray atomizing device that sprays at a constant rate, wherein the essence concentrate for facial or skin care, carrying negative ions, is sprayed on the skin through nano-electrospray ionization. The essence concentrate can be absorbed by the skin easily and the shortcoming in a conventional electrospray atomizing device that it cannot spray at a constant rate can be removed, with that the essence concentrate can be sprayed at a constant rate at each electrospray.

To enable a further understanding of said objectives and the technological methods of the invention herein, a brief description of the drawings is provided below followed by a detailed description of the preferred embodiments.

BRIEF DESCRIPTION OF THE DRAWINGS

FIG. 1 shows a three-dimensional schematic view of a main unit facing upward, according to the present invention.

FIG. 2 shows a three-dimensional schematic view of a main unit facing downward, according to the present invention.

FIG. 3 shows a planar perspective view on a bottom of the present invention.

FIG. 4 shows a planar perspective view on a side of the present invention.

FIG. 5 shows a cutaway schematic view of an action that ambient essence concentrate is sucked in, according to the present invention.

DETAILED DESCRIPTION OF THE PREFERRED EMBODIMENTS

Figure 1:
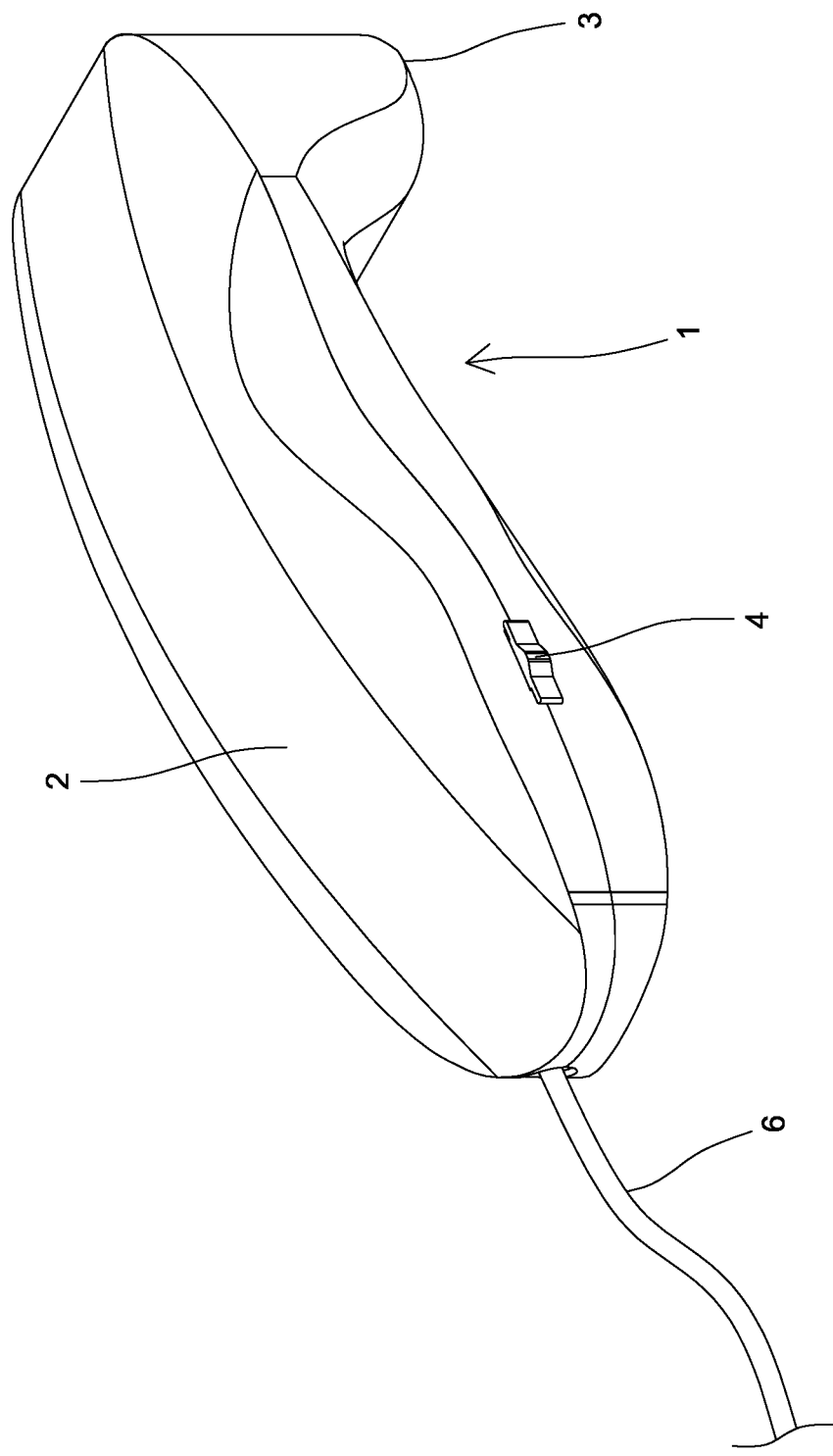
Figure 2:
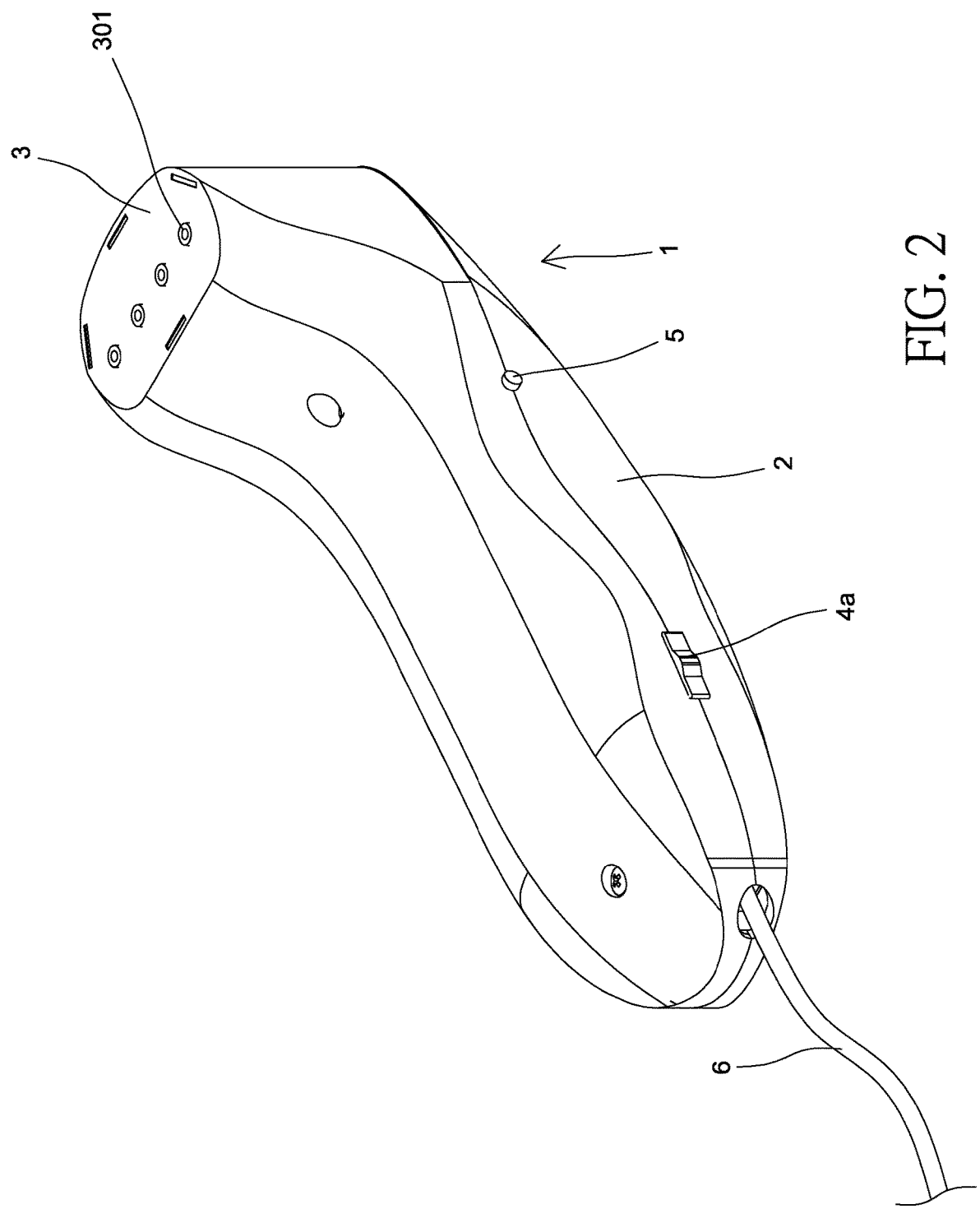
Figure 3:
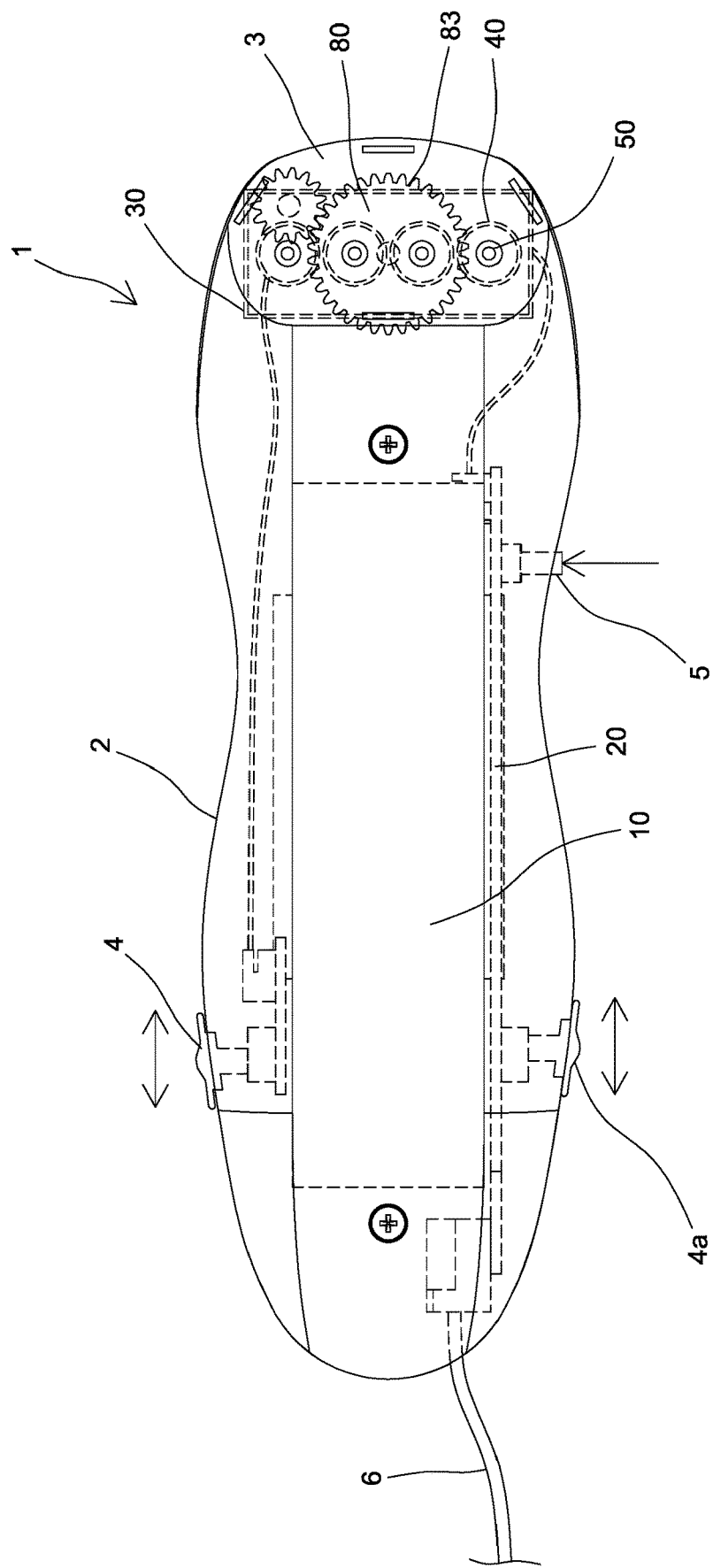
Figure 4:
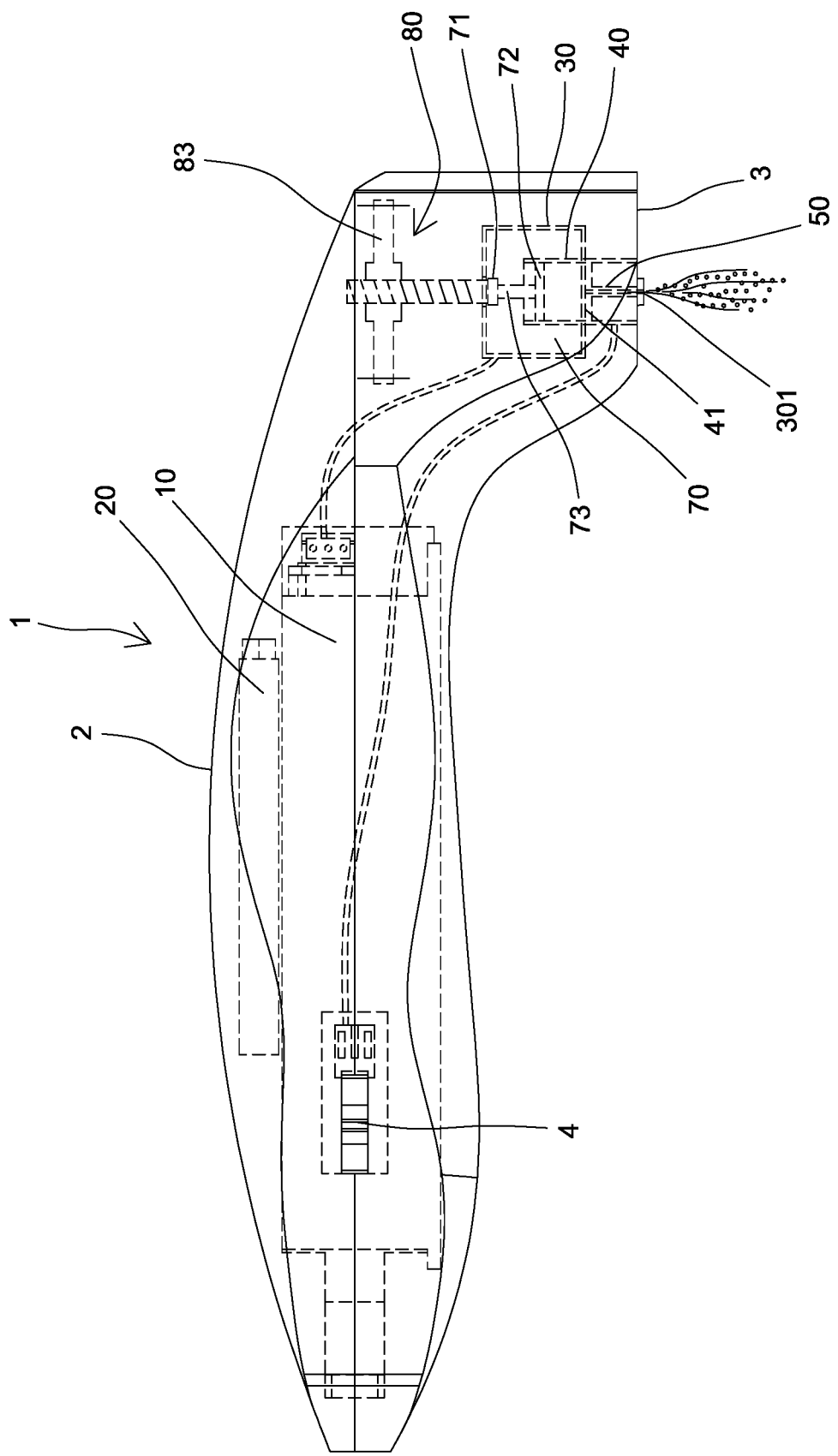
Figure 5:
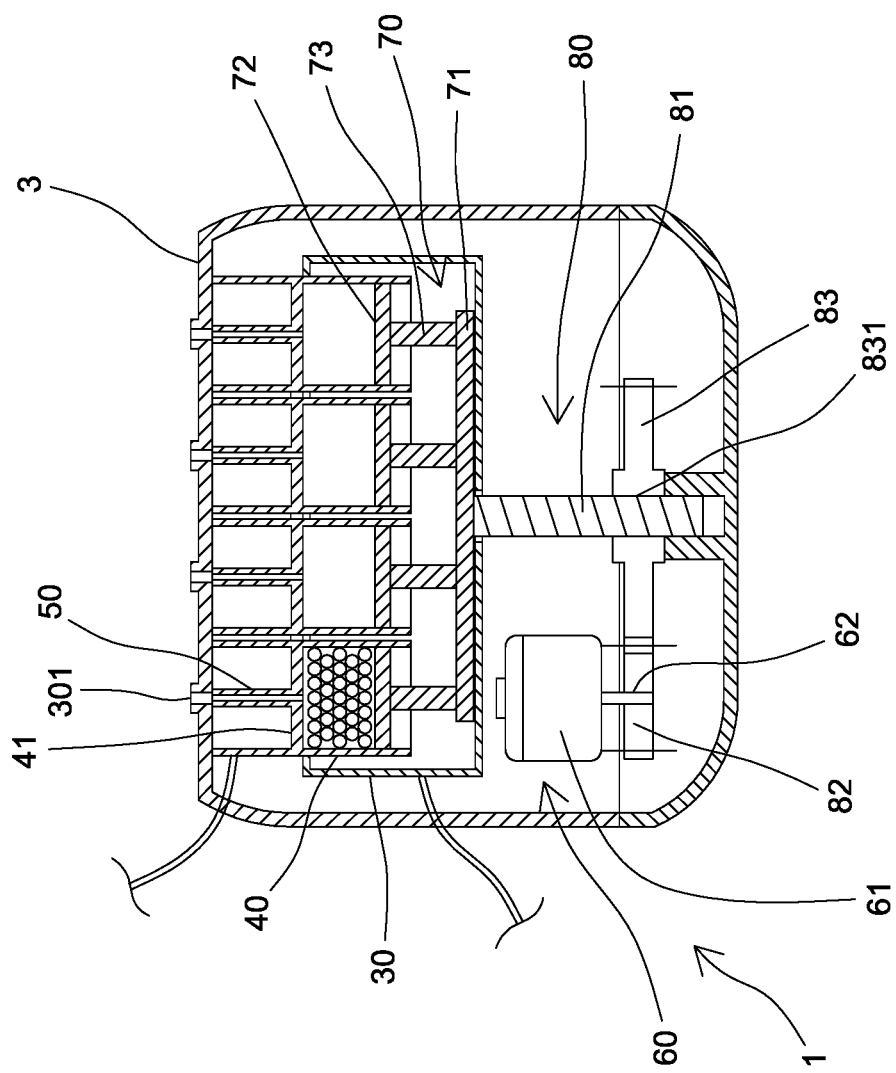
Figure 6:
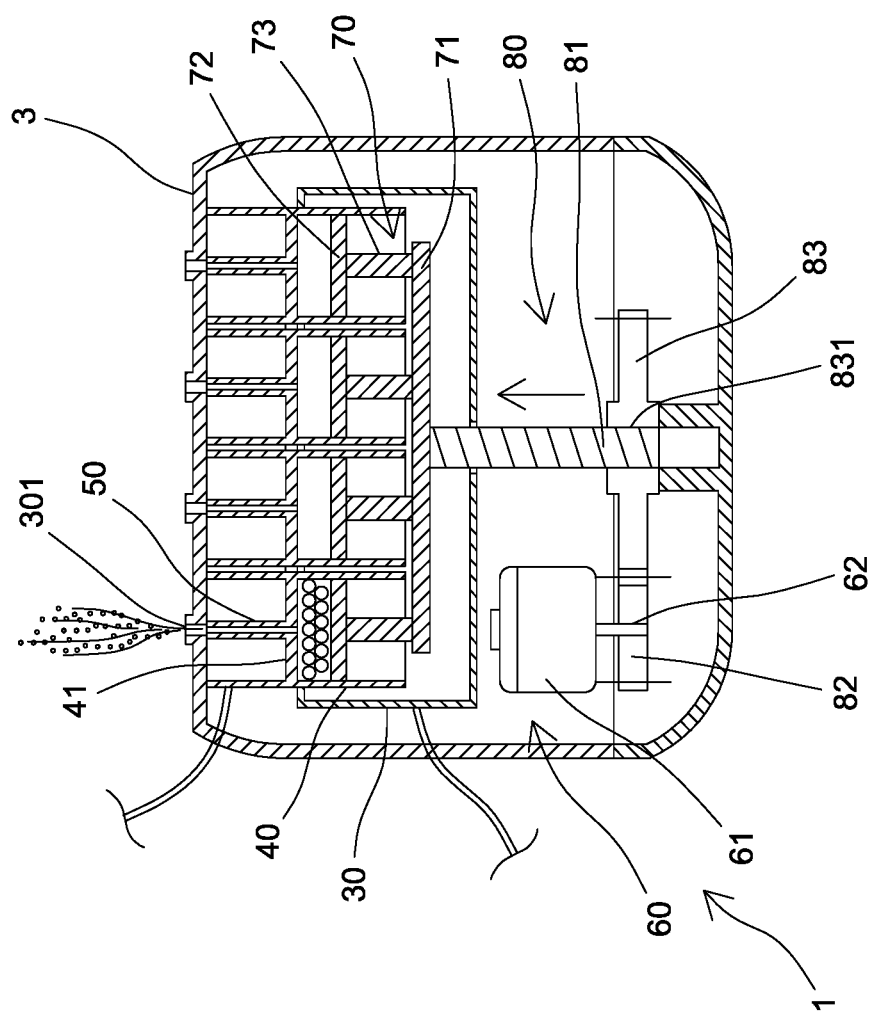
FIG. 6 shows a cutaway schematic view of an action of electrospray to the essence concentrate, according to the present invention.
Figure 7:
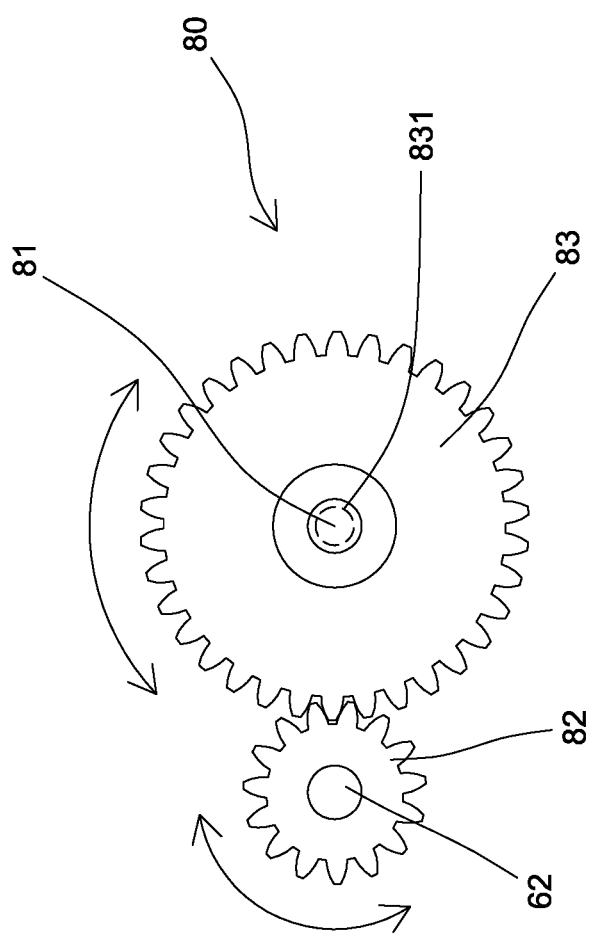
FIG. 7 shows a planar schematic view of a speed changer, according to the present invention.

Referring to FIGS. 1 to 7, the present invention comprises a main unit 1 which is provided with a handle 2 and a nozzle 3. The handle 2 is held by a hand and is provided with a first push button 4, a second push button 4a and a switch 5. The nozzle 3 is disposed on an upper side of the handle 2 for sucking in liquid (essence concentrate) and spraying out mist. An interior of the main unit 1 includes a transformer 10, a circuit board 20, an electrode plate 30, plural liquid tanks 40, plural syringes 50, a power mechanism 60 (as shown in FIGS. 5 to 7) and a dosing device 70. The main unit 1 can be connected externally with a power cord 6 (or the interior of the main unit 1 can be provided with batteries), and the power cord 6 is connected to a power source which provides electricity to the transformer 10, the circuit board 20 and the power mechanism 60. The electrode plate 30 is a cylinder and an interior of the electrode plate 30 is provided with the plural liquid tanks 40 which are small sealed barrels. Above each liquid tank 40 is a top board 41 for sealing the liquid tank 40, and a syringe 50 is disposed above the top board 41. The syringe 50 is connected with the liquid tank 40 which can store liquid water (the essence concentrate for skin care). Electric current flows to the electrode plate 30 and the syringes 50. The transformer 10 drives the circuit on the circuit board 20 to increase the driving voltage which is converted into high voltage having a negative polarity through a rectifier circuit, and is then applied onto the syringes 50 (negative electrode), releasing electrons to result in the negative ions. When the liquid water flows through the syringes 50, it will become mist and carry the negative ions. The power mechanism 60 includes a motor 61, the motor 61 is provided with a transmission shaft 62, the transmission shaft 62 rotates a speed changer 80, and the speed changer 80 drives a screw 81 to ascend or descend. The speed changer 80 is provided with a small gear 82 and a large gear 83, and a center of the small gear 82 is connected with the transmission shaft 62 of the motor 61, whereas the transmission shaft 62 drives the small gear 82 and then the large gear 83. A center of the large gear 83 is provided with a threaded hole 831, and when the large gear 83 rotates, the threaded hole 831 rotates simultaneously to ascend or descend the screw 81. The first push button 4 of the handle 2 controls the motor 61 to rotate clockwise, whereas the second push button 4a of the handle 2 controls the motor 61 to rotate counterclockwise. The switch 5 of the handle 2 turns on the power, and an upper side of the screw 81 is pivoted with and abutted to a push board 71. The dosing device 70 includes pistons 72, the push boards 71 and the liquid tanks 40. A piston 72 is disposed on a bottom of a liquid tank 40 and a liquid tank 40 is provided with a top board 41 for sealing the liquid tank 40. Above a top board 41 is a syringe 50 which is connected with a liquid tank 40. A post 73 is disposed between the piston 72 and the push board 71, and the nozzle 3 of the main unit 1 is provided with plural pinholes 301 (as shown in FIG. 2 and FIG. 5) which are opposite to the syringes 50. The pistons 72 are linked by the push boards 71 to ascend or descend, and when the pistons 72 ascend by the power mechanism 60, the liquid in the liquid tanks 40 will be sprayed out through the syringes 50, forming mist which carries the negative ions. On the other hand, when the pistons 72 descend by the power mechanism 60, the ambient liquid will be sucked into the liquid tanks 40 through the syringes 50 to wait for a next electrospray.

By the abovementioned structures, upon operating the present invention, the switch 5 of the handle 2 is pressed down to turn on the power, and the pinholes 301 of the nozzle 3 are immersed into the essence concentrate (by using a cup unit to store the essence concentrate, and enabling the pinholes 301 of the nozzle 3 to touch the essence concentrate in the cup unit). At this time, the first push button 4 is pushed, and the motor 61 is controlled to rotate clockwise. The transmission shaft 62 of the motor 61 rotates the small gear 82, and the then the small gear 82 drives the large gear 83. When the large gear 83 rotates clockwise, the thread hole 831 will rotate simultaneously to descend the screw 81. As the pistons 72 are acted upon by the power from the power mechanism 60, the screw 81 will descend. In addition, as the pressure in the liquid tanks 40 is small, the essence concentrate will be sucked into the liquid tanks 40 through the syringes 50. Next, the nozzle 3 is made to align with the skin, and then the second push button 4a is pushed to control the motor 61 to rotate counterclockwise. The transmission shaft 62 of the motor 61 then rotates the small gear 82 counterclockwise, whereas the small gear 82 drives the large gear 83. When the large gear 83 rotates counterclockwise, the threaded hole 831 will rotate simultaneously to ascend the screw 81. As the pistons 72 are acted upon by the power of the power mechanism 60, the screw 81 will ascend. In addition, as the pressure in the liquid tanks 40 is large, the essence concentrate in the liquid tanks 40 will be withdrawn and sprayed out through the syringes 50. Thus, the operation is repeated back and forth to withdraw the essence concentrate at a constant rate and spray out the atomized essence concentrate at a constant rate.

In the meantime, the transformer 10 drives the circuit on the circuit board 20 and increases the driving voltage which is converted into high voltage having a negative polarity through a rectifier circuit, and is then applied onto the syringes 50 (negative electrode), releasing electrons to result in the negative ions. When the essence concentrate flows through the syringes 50, it will become tiny atomized mist (forming nanosized mist), easily absorbed by human body.

In the present invention, the essence concentrate is taken out by electrospray ionization, forming nanosized mist of the essence concentrate which carryies the negative ions. Besides that, the essence concentrate is sucked in and sprayed out at a constant rate by the dosing device 70, which solves the shortcoming in the prior art that the conventional essence concentrate is coarse and also solves the shortcoming in the prior art that the conventional essence concentrate cannot be sprayed out at a constant rate at each spray. Furthermore, as the essence concentrate is stored outside the atomizer and is sucked in when needed, it can be sucked and sprayed in real time, which avoids the problem of getting contaminated or breeding fungi when the essence concentrate is stored in the atomizer.

It is of course to be understood that the embodiments described herein is merely illustrative of the principles of the invention and that a wide variety of modifications thereto may be effected by persons skilled in the art without departing from the spirit and scope of the invention as set forth in the following claims.

What is claimed is:

1. An electrospray atomizing device that sprays at a constant rate, comprising:

a main unit which contains a transformer, a circuit board, an electrode plate, plural liquid tanks, and plural syringes, wherein the electrode plate includes the plural liquid tanks, the plural syringes are disposed above the plural liquid tanks, the plural liquid tanks contain liquid water, the circuit board connects electric current to the electrode plate and the plural syringes, with that when the liquid water flows through the plural syringes, the liquid water becomes mist and carries negative ions;

wherein the electrospray atomizing device that sprays at a constant rate comprises:

a power mechanism, and a dosing device, wherein the power mechanism is provided with a motor, the motor is provided with a transmission shaft, the transmission shaft rotates a speed changer, the speed changer drives a screw to ascend or descend, an upper side of the screw is pivoted with and abutted to a push board, wherein the dosing device is provided with plural pistons on a bottom of the plural liquid tanks, the plural liquid tanks are provided with plural top boards for sealing the plural liquid tanks, the plural syringes are disposed above the plural top boards and are connected with the plural liquid tanks, and the plural pistons are linked by the push board to ascend or descend, with that when the plural pistons ascend by the power mechanism, the liquid water in the plural liquid tanks is sprayed out through the plural syringes to form mist which carries the negative ions, or when the plural pistons descend by the power mechanism, an ambient liquid outside of the electrospray atomizing device is sucked into the plural liquid tanks through the plural syringes to wait for a next electrospray.

2. The electrospray atomizing device that sprays at a constant rate, according to claim 1, wherein the speed changer is provided with a small gear and a large gear, a center of the small gear is connected with the transmission shaft of the motor to drive the small gear and then the large gear, a center of the large gear is provided with a threaded hole, and the threaded hole provides for ascending or descending the screw.

3. The electrospray atomizing device that sprays at a constant rate, according to claim 1, wherein pinholes are disposed on the main unit, opposite to the plural syringes.

4. The electrospray atomizing device that sprays at a constant rate, according to claim 1, wherein the main unit is connected externally to a power cord which is connected to a power source which provides electricity to the transformer, the circuit board and the motor.

5. The electrospray atomizing device that sprays at a constant rate, according to claim 1, wherein the transformer drives a circuit on the circuit board and increases a driving voltage which is converted into a high voltage having a negative polarity through a rectifier circuit and is then applied onto the plural syringes.

6. The electrospray atomizing device that sprays at a constant rate, according to claim 1, wherein the main unit is provided with a handle and a nozzle.

7. The electrospray atomizing device that sprays at a constant rate, according to claim 1, wherein plural posts are disposed between the plural pistons and the push board.

8. The electrospray atomizing device that sprays at a constant rate, according to claim 6, wherein the handle is provided with a first push button, a second push button and a switch.

* * * * *